United States Patent [19]

Haag et al.

[11] 4,300,009

[45] Nov. 10, 1981

[54] CONVERSION OF BIOLOGICAL MATERIAL TO LIQUID FUELS

[75] Inventors: Werner O. Haag, Lawrenceville; Paul G. Rodewald, Rocky Hill, both of N.J.; Paul B. Weisz, Yardley, Pa.

[73] Assignee: Mobil Oil Corporation, New York, N.Y.

[21] Appl. No.: 150,109

[22] Filed: May 15, 1980

Related U.S. Application Data

[63] Continuation of Ser. No. 974,205, Dec. 28, 1978, abandoned.

[51] Int. Cl.$^3$ .................. C07C 11/20; C07C 11/32; C07C 1/00
[52] U.S. Cl. .................. 585/408; 585/240; 585/241; 585/357; 585/469; 585/638; 585/640; 585/733
[58] Field of Search .............. 585/240, 241, 357, 408, 585/469, 638, 640, 733

[56] References Cited

U.S. PATENT DOCUMENTS

| | | | |
|---|---|---|---|
| 1,680,908 | 8/1928 | Nishida | 585/241 |
| 3,936,353 | 2/1976 | Chen | 585/240 |
| 4,102,938 | 7/1978 | Rao | 585/240 |

*Primary Examiner*—Curtis R. Davis
*Attorney, Agent, or Firm*—C. A. Huggett; M. G. Gilman; V. J. Frilette

[57] ABSTRACT

Living plants and animals synthesize and often accumulate a wide variety of organic materials having a molecular weight greater than 150. These include different chemical types such as natural hydrocarbons including rubbery substances, natural resins, and natural glycerides such as oils and fats. These substances, formed in the anabolic process, are collectively called "anabolites".

This invention provides a process for catalytically converting certain anabolites to liquid hydrocarbons useful for the manufacture of fuels such as gasoline and chemicals such as para-xylene. Crystalline aluminosilicate zeolites having an effective pore size of greater than about 5 Angstrom units are useful catalysts.

17 Claims, No Drawings

CONVERSION OF BIOLOGICAL MATERIAL TO LIQUID FUELS

CROSS-REFERENCE TO RELATED APPLICATIONS

This application is a continuation of copending U.S. Patent Application Ser. No. 974,205 filed Dec. 28, 1978, now abandoned.

BACKGROUND OF THE INVENTION

1. Field of the Invention

This invention is concerned with the conversion of biological material to hydrocarbons. More particularly, it is concerned with the manufacture of hydrocarbon fuels and chemicals from organic products produced by plants and animals. By the process of this invention, such organic products are catalytically transformed to high quality fuels and chemicals. This invention is further concerned with a catalytic process whereby raw material produced by living matter is converted to gasoline or other liquid hydrocarbon fuel with high energy effiency.

2. Prior Art

There is currently a lively interest in finding economical sources other than petroleum for liquid fuels and hydrocarbon chemicals. It is well known, of course, that methanol may be produced from coal and ethanol by fermentation of sugars. However, both of these processes are costly and considerably more than one gallon of alcohol is needed to provide the energy available from a gallon of liquid hydrocarbon such as fuel oil. Gasoline may be made from coal, but again the cost is high and the gasoline as produced is of poor quality.

Several unconventional ideas have been proposed to convert plant materials to fuels and chemicals. A summary of these proposals is listed in a chapter entitled "Fuels and Chemicals from Crops" in the book by L. L. Anderson and D. A. Tillman "Fuels from Waste", Academic Press, New York, 1977; the entire contents of said chapter is incorporated herein by reference for background purposes. The processes include anaerobic digestion to produce methane, fermentation, gasification and pyrolysis.

In general, the prior art processes suffer from several disadvantages. They usually produce a plurality of product streams that require separate handling, by-products of low value, and a stream that requires disposal. For example, anaerobic fermentation, in addition to methane, yields a solid sludge and a waste liquid stream. Pyrolysis of wood produces a mixture of organic compounds, gases, tars and char, as well as a contaminated aqueous stream. Fermentation of starch or sugar can yield ethanol, acetone, butanol or a number of other organic chemicals. However, since fermentation requires the desired product to be formed in dilute aqueous solution, distillation is required which is not only costly but also requires considerable energy. As a result, the net yield of useful fuel or chemicals that may be realized from an acre of agricultural effort by fermentation is quite limited.

For example, in ethanol production from corn, the typical total biomass of corn growth on an acre may have a fuel value equivalent to 600 gallons of gasoline. The fermentation and distillation sequence yields only about 25% of that energy, or ethyl alcohol product equivalent to 150 gallons of gasoline. The fermentation-distillation sequence itself requires fuel, and this fuel requirement can exceed the amount of fuel value produced as alcohol. New technology can reduce this fuel requirement, or it can conceivably be eliminated by using farm waste. However, the agricultural effort alone, including its industrial support (fertilizers, chemicals, tractors, machinery) requires fuel equivalent to about 92 gallons. Thus, while the apparent productivity is equivalent to 150 gallons of fuel (as ethanol) at the plant, the net amount won is only 58 gallons of fuel equivalent. In addition, corn production requires high quality agricultural land. In brief, there is evidently a need for efficient methods by which substances produced by plants or animals may be converted to high quality hydrocarbon fuels and chemicals.

BRIEF SUMMARY OF THE INVENTION

It has now been discovered that organic substances built up by plants or animals and having a certain prescribed composition and molecular weight as more fully described hereinbelow may be converted directly to useful hydrocarbons by catalytic conversion with a catalyst comprising a crystalline zeolite having a pore size greater than about 5 Angstroms.

For convenience, the term "anabolite" will be used herein to designate a substance which is produced by constructive metabolism in a plant or an animal. In the process of this invention, the plant or animal anabolite or mixture thereof is segregated from the plant or animal by any suitable means, and is then contacted under conversion conditions with the described catalyst at a temperature of 300° to about 650° C. to form a hydrocarbon mixture useful for liquid fuels and chemicals. In particular, at least 50 percent of the liquid hydrocarbons so produced distill at a temperature below about 170° C.

DETAILED DESCRIPTION OF THE INVENTION

Plants and animals generate an enormous variety of anabolites. These are organic materials which, in plants, are constructed from smaller molecules via photosynthesis. Plant anabolites include, for example, such widely divergent materials as sugars and cellulose, fats, chlorophyl, monocyclic, dicyclic and polycyclic terpenes, long chain alcohols, low molecular weight and high molecular weight polyisoprenoid hydrocarbons including natural rubber and gutta percha. This list is by no means exhaustive, but is merely indicative of the variety of structure and the diversity of molecular weight which can range from as low as a molecular weight of 16 (methane) to natural rubber with a molecular weight over 1 million.

Animals, like plants, generate a variety of anabolites which include proteins, fatty acids, fats, steroids, and a variety of modified triglycerides, such as lecithin. Whereas such materials ordinarily are not built up in the animal from very small molecules as in photosynthesis, they nevertheless involve the metabolic process of the animal in modifying and reconstituting constituents of the animal feed such that products are produced by the animal which are needed for survival of the particulr animal or its species.

The anabolites contemplated as useful for purposes of the present invention are those that have a molecular weight greater than 150. Many anabolites such as fatty oils have molecular weights substantially greater than 150, i.e. 500 or higher. Some anabolites, such as natural rubber, may have a molecular weight greater than 100,000.

Anabolites suitable as feed for the process of this invention are characterized by an effective hydrogen to carbon ratio of about 1 to 2.2. The effective hydrogen to carbon ratio, abbreviated herein as $(H/C)_{eff}$, is calculated from the gross composition as follows:

$$(H/C)_{eff} = \frac{H - 2O - 3N - 2S}{C}$$

where H, C, O, N, S are the relative atom ratios of hydrogen, carbon, oxygen, nitrogen and sulfur as determined by elemental analysis of the feed on an anhydrous basis.

To illustrate the computation of $(H/C)_{eff}$, i.e. the effective hydrogen to carbon ratio, of butter from cows, for example, an elementary analysis of a sample, on an anhydrous basis, would give the approximate empirical formula with no significant nitrogen or sulfur content as follows:

$$C_{8.5}H_{16.3}O$$

Inserting the appropriate values in the above equation gives:

$$(H/C)_{eff} = \frac{16.3 - 2 - 0 - 0}{8.5} = \frac{14.3}{8.5} = 1.68$$

Randon examples of suitable anabolites are:

|  | Analysis | (H/C) eff |
|---|---|---|
| Butter fat (Cow's) | $C_{8.5}H_{16.3}O$ | 1.68 |
| Terpenes, natural rubber | $(C_5H_8)_n$ | 1.60 |
| Resin acids | $C_{20}H_{30}O_2$ | 1.30 |
| Stearin | $C_{57}H_{110}O_6$ | 1.72 |
| Palmitin | $C_{51}H_{98}O_6$ | 1.69 |
| Cholesterol | $C_{27}H_{46}O$ | 1.63 |

Materials that have $(H/C)_{eff}$ less than 1 are in general not suited since they give only low yields of desired premium fuels and chemicals; in addition, they cause rapid loss of catalytic activity. Examples of such materials are sugars, starches, cellulose, peat, and lignin.

|  | Analysis | (H/C) eff |
|---|---|---|
| Sugar | $C_{12}H_{22}O_{11}$ | 0 |
| Starch, cellulose | $(C_6H_{10}O_5)_n$ | 0 |
| Pet (air dried | C 26.39% | 0.24 |
|  | H 2.77 |  |
|  | O 15.63 |  |
|  | N 1.23 |  |
|  | S .12 |  |
|  | Moisture 50 |  |
|  | Ash 3.86 |  |

For purposes of this invention, it is preferred to use anabolites characterized by an $(H/C)_{eff}$ of at least 1.3 for improved efficiency. Most of the anabolites currently or potentially available in substantial quantity have an $(H/C)_{eff}$ in the range of about 1.3 to about 1.8.

In the practice of the present invention, a suitable plant or animal anabolite is prepared by segregation from the plant or animal. As used in this specification, the term "segregation" is used to cover all conventional means for isolating the anabolite prior to its use as feed to the catalytic conversion step. For example, olives may be harvested and pressed to segregate olive oil, a suitable anabolite. Or, as illustrated by the technique used to obtain gum naval stores and natural hevea rubber, the plant may be wounded by incision and the exudate collected. In still another method, the plant material may be shredded and pressed or extracted with suitable solvents such as acetone, benzene, petroleum solvents and the like. All of these methods and others are contemplated as encompassed within the term "segregation" as used herein. It is noteworthy that in some instances the plant is sacrificed in the segregation step, while in other instances it is not. A similar situation applies to animal-derived anabolites; butter fat may be obtained simply by milking the cow followed by separation of cream and churning, in which case the animal remains productive; or tallow, another suitable anabolite, is obtained as a slaughterhouse by-product.

Segregation, as used herein, may be incidental in that it is practiced in connection with another process. The production of tallow is one illustration. The production of tall oil (a mixture of rosin acids and oleic acid) incidental to paper making is another instance. Tall oil is contemplated as a suitable anabolite.

It should be noted that, in describing the process of this invention, reference sometimes is made to butter fat and other edible materials. These references are made only as convenient illustrations and do not imply that the process of this invention need or should be practiced at the expense of an ample food supply. On the contrary, it is envisioned that the fuels made by the process of this invention will be available for agricultural use thereby sustaining the supply.

It is to be understood that for purposes of this invention mixtures of anabolites, albeit of different chemical types such as fat and hydrocarbon, are suitable as feed to the catalytic conversion step. Thus, mixtures of plant anabolites, mixtures of animal anabolites, and mixtures which include both plant and animal anabolites are within the scope of this invention provided that the mixtures have, on an anhydrous basis, a molecular weight (i.e. a weight average molecular weight) of greater than 150 and also have an $(H/C)_{eff}$ ratio of about 1/1.0 to 2.2/1.0. It is a feature of this invention that the segregated anabolite need not be in anhydrous or pure form. Indeed, as will be further illustrated hereinbelow and by examples, the segregated anabolite may be in the form of a dispersion in water, such as is the case for natural rubber latex, and it may be accompanied by minor amounts of protein, sugar and minerals. Such aqueous dispersions are directly converted catalytically in the process of this invention with high overall energy efficiency since the water is easily decanted from the hydrocarbon product after conversion.

Three particular types of anabolites are particularly suited for the process of this invention because they are currently or potentially available in substantial quantity and are efficiently catalytically converted in the process of this invention. These types are the natural hydrocarbons, the natural resins, and the natural glycerides.

The natural hydrocarbons include most prominently natural rubber obtained from rubber trees of the *Hevea brasiliensis* type. Many of the plants that generate hydrocarbons or near-hydrocarbons belong to the Euphorbiaceae family, the majority of whose members carry a milky juice or latex. Examples are found among the genera Hevea, Manihot, Mabea and Sabium, certain species of which contain hydrocarbons suitable for rubber production. Other plant genera include Ricinus, Asclepias (milkweed), Solidago (Goldenrod) and Euphorbia. The latter is a particularly prolific hydrocarbon-bearing plant genus. (See Chemtech, Vol. 7, pp. 352 ff., 1977). Melvin Calvin has pointed out that E. lathyrus (gopher plant) and E. tirucalli (aveloz, milk bush), are potentially attractive plants for generating hydrocarbon-like constituents. Other examples are E. resinifera, E. trigona and E. cerifera (candelilla). The wax produced by E. cerifera is composed of hydrocarbons (about 50%, mostly hentriacontane), and a mixture of fatty acids, terpenoid esters and alcohols. Another plant that produces rubber-like hydrocarbons is the guayule that grows in Mexico and the Southern U.S.

These plant-derived hydrocarbons are usually accompanied by proteins, sugars and other carbohydrates, steroids, and minerals, i.e. compounds containing the heteroatoms oxygen, nitrogen and sulfur, among others, in functional groups such as oxy, hydroxy, carboxy and amino groups. Furthermore, many materials are viscous liquids or rubber-like near-solids. In any event, most often their molecular weight is not in the liquid fuel range, but typically several thousand to several millions. These properties make them unsuitable as liquid fuels. While it has been suggested to pyrolize such materials to smaller molecular weight products, such processes are highly endothermic and are carried out at very high temperature, thus requiring a substantial energy input. In addition, the resulting cracked products cannot be used directly as premium fuels. They are directly convertible to high grade fuels such as high octane gasoline by the process of this invention, however.

The hydrocarbon substance can be catalytically converted in crude form. For example, the rubber latex from *Hevea brasiliensis* is an aqueous suspension containing 30-40 weight % of rubber. The crude rubber consists, by weight, of about 86.5% polyisoprene rubber, 5% protein, 5% acetone soluble organic matter, 1.5% methyl inositol, 0.5% sugars and 1.5% minerals. As illustrated below, the whole aqueous latex is converted without any prior separation, to form valuable fuels and chemicals; the aqueous by-product stream is of such purity as to cause no disposal problems.

The second type of anabolite is the natural resins. These may be hydrocarbons, but in most instances the structure, where known, contains carboxyl groups, hydroxyl groups, and sometimes ester groups. Illustrations of the natural resins include gum and wood rosin, one of the principal constituent thereof being abietic acid. Abietic acid consists of a polycyclic hydrocarbon moiety and a carboxyl moiety. It has a molecular weight of 302. Other natural resins include shellac, dammar, copal, and sandarac.

A third type of anabolite particularly suited is characterized herein as the natural glycerides. These substances are widely produced in substantial quantities by animals and plants and are characteristically triglycerides of fatty acids containing from 4 to 20 carbon atoms, the fatty acids most commonly being saturated or containing 1, 2, or 3 double bonds. Some of these are edible, among which are corn oil, soybean oil, cottonseed oil, olive oil, peanut oil, tallow and butter. Castor oil is an example of an inedible oil. Oils used industrially and not generally considered edible include linseed, oiticica and tung oils. Contemplated as within the scope of the natural glycerides are triglycerides which contain two fatty acids, the third esterified group being a phosphatide, of which lecithin is an example.

Natural esters other than triglycerides also may be used in the process of this invention. Jojoba oil, for example, may be used. This oil is composed principally of simple esters of unsaturated fatty acids and alcohols, each of which has from 18 to 24 carbon atoms. Yellow beeswax and bayberry wax are further examples of such natural esters.

In one preferred embodiment of this invention, an anabolite selected from the group consisting of natural hydrocarbons, natural resins, and natural glycerides is segregated and catalytically converted in the process of this invention.

As described herein, the segregated anabolite or mixture thereof need not be of high purity. Also, a wide variety of means may be employed in the segregation step. For example, in the case of a hydrocarbon latex, it is contemplated as within the scope of this invention to first separate the latex material into various fractions. For example, latex from rubber producing plants can be separated into aqueous serum and crude rubber, for example, by coagulating the latter thermally, or chemically by addition of carboxylic acids and the like. The crude rubber is then pressed to remove serum and processed separately according to this invention. The hydrocarbon-rich material can also be separated by solvent extraction of the latex, especially if it is of lower molecular weight than that contained in rubber plants. The particular choice of processing depends mostly on economic factors. Processing crude latex is a simple operation and requires a lower capital investment. On the other hand, processing only the crude hydrocarbon fraction results in an increased thermal efficiency of the conversion process.

It is further contemplated that either the whole or only a portion of the hydrocarbon substance be processed according to this invention. For example, the guayule (parthenium argentatum) latex can be separated into a rubber fraction and a resin fraction. It may be desirable to recover the rubber as such and process the resin fraction only.

In all cases, it is to be emphasized that the anabolite or mixture thereof that is contacted with catalyst according to this invention is one which has a weight average molecular weight greater than 150, and also is characterized by a $(H/C)_{eff}$ on an anhydrous basis of about 1/1.0 to 2.2/1.0.

The catalyst useful in this invention comprises a crystalline aluminosilicate zeolite having an effective pore diameter greater than about 5 Angstrom units as evidenced by its ability to sorb benzene. A number of such zeolites are known and include, by way of example, zeolite X, zeolite Y, offretite and mordenite. For purposes of this invention, the zeolite is preferably at least partially in the hydrogen form and may contain rare earth cations. The preparation of a cracking catalyst comprising rare earth exchanged zeolite X dispersed in a matrix of silica-alumina is described in U.S. Pat. Nos. 3,140,249 and 3,140,253 issued July 7, 1964, the entire contents of which are incorporated herein by reference.

The particularly preferred crystalline aluminosilicate zeolites which are highly effective when used in the process of this invention are members of a novel class of zeolites that exhibits unusual properties. Although these zeolites have unusually low alumina contents, i.e. high silica to alumina ratios, they are very active even when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have a low coke-forming activity and therefore are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The preferred zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Rather than attempt to judge from crystal structure whether or not a zeolite possesses the necessary constrained access to large molecules, a simple determination of the "Constraint Index" as herein defined may be made by passing continuously a mixture of an equal weight of normal hexane and 3-methylpentane over a small sample, approximately one gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of n-hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| CAS | C.I. |
| --- | --- |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Clinoptilolite | 3.4 |
| Beta | 0.6 |
| ZSM-4 | 0.5 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are preferred in the instant invention. The very nature of this parameter and the recited technique by which it is determind, however, admit of the possibility that a given zeolite can be tested under somewhat different conditions and thereby have different Constraint Indexes. Constraint Index seems to vary somewhat with severity of operation (conversion) and the presence of absence of binders. Therefore, it will be appreciated that it may be possible to select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of preferred zeolites defined herein is exemplified by ZSM-5, ZSM-11, ZSM-12, ZSM-23, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the pressure of these cations does appear to favor the formation of this special class of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-23, ZSM-35, and ZSM-38, with ZSM-5 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Amgstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 5 to about 80 percent by weight of the dry composite.

Contacting the segregated anabolite or mixture thereof with the catalyst in the process of this invention may be carried out with a fixed catalyst bed, or a fixed fluid bed, or a catalyst bed operated in a transport fashion such that the catalyst, whether or not fluidized, is cycled between a reaction zone and a regeneration zone, as is currently practiced in the fluid catalytic cracking of petroleum gas oils. In a fixed or moving bed operation, the average particle size of the catalyst may be as great as one-half inch or more, but is generally between one-sixteenth and one-fourth of an inch in diameter. If a fluid bed is employed, the catalyst must be in finely divided form which can be fluidized by the lifting action of the feed vapors. The solid catalyst may also be held in fluidized form by a stream of relatively inert gas such as steam, $CO_2$, CO, flue gas, $N_2$, He or methane, and the feed is introduced in fluid or solid form. With a latex feed, for example, the vaporization of the water on contact with the hot catalyst bed will serve to maintain the fluidized bed in suspended state. The anabolite feed is passed over the catalyst at a rate of 0.2–20 WHSV (weight hourly space velocity) preferably at 0.5 to 5.0 WHSV. In all cases, the WHSV is calculated on the pounds of anhydrous anabolite fed per hour per pound of catalyst in the bed. For purposes of this invention, the anabolite fed is contacted with the catalyst at a pressure of 1 to 50 atmospheres absolute, and preferably at a pressure of 0 to 150 p.s.i.g. (pounds per square inch gauge). In all cases, the conversion is conducted at a temperature of 300° to about 650° C. In general, the reaction conditions may be adjusted within the prescribed limits to vary the character of the product. The contacting is conducted in all cases within the prescribed limits under such combination of conditions that the liquid hydrocarbon mixture which is formed and recovered contains at least 40 volume percent of components which distil below 170° C. when the liquid hydrocarbon product is subjected to atmospheric fractional distillation by methods well known to those skilled in the art. In general, if it is desired to recover liquid hydrocarbon containing a substantial fraction of aromatic hydrocarbons, as compared with paraffin, olefin, and naphthenic hydrocarbons, this may be achieved by a modest increase in the severity of the operation, induced by increased temperature, and/or decreased space velocity. Likewise, if it is desired to recover increased amount of liquid hydrocarbons of the non-aromatic type, this is achieved by a decrease in the severity of the contacting step.

In general, the effluent from the contacting step, which is at high temperature, is cooled to about room temperature, thereby recovering a mixture of normally liquid hydrocarbons that have 4 or more carbon atoms. When the particularly preferred catalysts of this invention are used, the recovered liquid hydrocarbon mixture will contain a very large fraction in the gasoline boiling range of 32.2° to 221° C., and in some instances all of the liquid hydrocarbon mixture will be in this boiling range. This recovered liquid hydrocarbon mixture contains a significant fraction of benzene, toluene, and xylenes, which may be separated by methods known in the art, and used as petrochemicals, feedstock or as aromatic solvents. In a particularly preferred embodiment of this invention, wherein a crystalline aluminosilicate zeolite having a silica/alumina ratio to at least about 12, and a constraint index of about 1 to 12 is used, the recovered liquid hydrocarbon product contains a significant amount of toluene, at least 5% by volume, and may contain 20 volume percent or more toluene. It is noteworthy that the anabolites of this invention contain substantially less than 5% toluene; in fact, toluene is usually undetectable as a component thereof.

Contemplated as within the scope of this invention is to conduct the contacting step in the presence of hydrogen gas which, in some instances, serves to prolong catalyst life.

Another variant of the process contemplated and within the scope of this invention is to feed to the catalyst a segregated anabolite together with a solvent comprised of material which, itself, is substantially inert to thermal or catalytic decomposition. This can also be done by having solvent molecules of such size and shape that they are incapable of penetrating the zeolite catalyst pores and of a structure that imparts inertness. Examples are liquids such as substituted naphthalene or phenanthrene. Also, we may use catalytically substantially inert liquids such as cycle stocks, or fractions thereof, from catalytic cracking operations.

Particularly with very high molecular weight anabolites such as rubber, it is advantageous to conduct the contacting step in a manner such that the temperature of the anabolite is raised to reaction temperature quickly. This is most conveniently accomplished by utilizing the catalyst itself as the principal heat source, in which case the formation of undesirable refractory coke-like material is minimized.

As discussed hereinabove, the liquid hydrocarbon mixture produced by the described process may be fractionated to produce gasoline and kerosine, and/or aromatic hydrocarbons useful as chemicals. It is interesting to note that although the individual hydrocarbon compounds found in the fractions are chemically the same as those found in equivalent petroleum-derived fractions, their high content of isotopic carbon-14 compared with the petroleum compounds is evidence that they are formed from non-fossil materials.

The following examples are given only to illustrate this invention and are not to be construed as limiting the invention. All parts shown in the examples are by weight unless specified otherwise. In the examples which follow, the notations P, O and A are used to designate types of hydrocarbons as follows:

P signifies "paraffins"
O signifies "olefins"
and A signifies "aromatics".

EXAMPLE 1

Natural rubber latex (Hevea Braziliensis) was coagulated by adding 75 cc iso-propylalcohol to 50 cc latex. The coagulum was separated, rinsed with distilled water, and pressed out into a sheet approximately 1–5 mm in thickness. The sheet was then cut into slivers of rubber 5 mm in width and 10 mm in length.

A 5.0 g quantity of this rubber was placed in a glass pyrolyzer tube and heated to 320° under flowing nitrogen. The pyrolysis gases were entrained with nitrogen and passed through a fixed bed of 1.0 g HZSM-5 catalyst maintained at 371° C. and one atmosphere pressure. The reaction product was condensed using a cold water condenser to produce a liquid having the following aromatics rich hydrocarbon distribution, as determined by gas chromatography.

| Component | Wt % | Component | Wt % |
|---|---|---|---|
| Methane | 0.0 | $C_5 P + O$ | 0.1 |
| Ethane | 0.0 | $C_6 P + O$ | 3.2 |
| Ethylene | 0.0 | $C_7$–$C_8 P + O$ | 19.9 |
| Propane | 0.0 | Benzene | 2.4 |
| Propylene | 0.0 | Toluene | 25.4 |
| i-Butane | 0.2 | Ethylbenzene | 4.3 |
| n-Butane | 0.1 | Xylenes | 25.1 |
| Butenes | 0.5 | $C_9^+ P + O + A$ | 18.8 |

EXAMPLE 2

Syntower bottoms obtained from a catalytic cracking unit were distilled under vacuum. The fractions boiling at 200°–290° C. at 10 mm Hg pressure were combined and used as a solvent for rubber. The rubber was prepared as in Example 1.

A 5% solution of rubber in distilled syntower bottoms was pumped at 0.5 WHSV over a fixed bed of 1.50 g HZSM-5 catalyst maintained at 482° C. and 200 psig. The reaction product was condensed using a cold water condenser to give a liquid having the following hydrocarbon distribution (exclusive of solvent) as determined by gas chromatography.

| Component | Wt % | Component | Wt % |
|---|---|---|---|
| Methane | 0.0 | $C_5 P + O$ | 5.7 |
| Ethane | 0.0 | $C_6 P + O$ | 5.7 |
| Ethylene | 0.0 | $C_7$–$C_8 P + O$ | 4.1 |
| Propane | 3.2 | Benzene | 5.3 |
| Propylene | 0.0 | Toluene | 39.2 |
| i-Butane | 2.0 | Ethylbenzene | 2.3 |
| n-Butane | 3.0 | Xylenes | 14.7 |
| Butenes | 0.0 | $C_9^+ P + O + A$ | 14.6 |

EXAMPLE 3

Natural rubber latex was pumped at 0.6 WHSV over a fixed bed of 4.50 g HZSM-5 catalyst maintained at 482° C. and one atmosphere pressure. Liquids were condensed using a cold water condenser; gases were collected over brine. The following table shows the combined hydrocarbon product distribution as determined by gas chromatography.

| Component | Wt % | Component | Wt % |
|---|---|---|---|
| Methane | 0.4 | $C_5 P + O$ | 0.7 |
| Ethane | 0.0 | $C_6 P + O$ | 3.5 |
| Ethylene | 5.2 | $C_7$–$C_8 P + O$ | 4.9 |
| Propane | 3.2 | Benzene | 5.4 |
| Propylene | 9.6 | Toluene | 20.6 |
| i-Butane | 2.2 | Ethylbenzene | 2.6 |
| n-Butane | 0.9 | Xylenes | 24.8 |
| Butenes | 6.1 | $C_9^+ P + O + A$ | 10.0 |

EXAMPLE 4

A glass fluidized bed reactor was charged with 60 cc 60–80 mesh HSZM-5. The bed was fluidized with helium flowing at 820–880 cc/minute and was maintained at 400° C. and one atmosphere pressure. Rubber latex was pumped at 20 cc/hour directly into the fluidized bed. Products from the reactor were passed through ice water, dry-ice-acetone, and liquid nitrogen cooled traps in series. After 5 hours time on stream the reactor was shut down. The cold traps were warmed and the gases evolved were collected over brine. The liquids in the traps were combined. The following table shows the combined hydrocarbon product distribution as determined by gas chromatography.

| Component | Wt % | Component | Wt % |
|---|---|---|---|
| Methane | 0.0 | $C_5 P + O$ | 0.4 |
| Ethane | 0.0 | $C_6 P + O$ | 0.9 |
| Ethylene | 1.6 | $C_7$–$C_8 P + O$ | 4.8 |
| Propane | 0.3 | Benzene | 3.8 |
| Propylene | 2.4 | Toluene | 21.4 |
| i-Butane | 0.4 | Ethylbenzene | 3.4 |
| n-Butane | 0.1 | Xylenes | 27.6 |
| Butenes | 1.2 | $C_9^+ P + O + A$ | 31.7 |

EXAMPLE 5

A glass fluidized bed reactor was charged with 60.0 cc 60–80 mesh HZSM-5. The bed was fluidized with helium flowing at 1100–1200 cc/minute and was maintained at 400° C. and one atmosphere pressure. Rubber prepared as in Example 1 was cut into cubes approximately 5 mm on an edge and was fed at a rate of 7 g/hour directly to the fluidized bed through an interlock system designed to prevent loss of hydrocarbon product gases. The product was condensed as described in Example 4. The following table shows the observed hydrocarbon product distribution as determined by gas chromatography.

| Component | Wt % | Component | Wt % |
|---|---|---|---|
| Methane | 0.0 | $C_5 P + O$ | 3.0 |
| Ethane | 0.1 | $C_6 P + O$ | 3.5 |
| Ethylene | 1.5 | $C_7$–$C_8 P + O$ | 9.7 |
| Propane | 1.4 | Benzene | 3.5 |
| Propylene | 3.8 | Toluene | 16.7 |
| i-Butane | 2.6 | Ethylbenzene | 4.1 |
| n-Butane | 0.8 | Xylenes | 22.4 |
| Butenes | 6.3 | $C_9^+ P + O + A$ | 20.6 |

EXAMPLE 6

Isoprene and water were pumped at 0.6 WHSV and 2.8 WHSV respectively over a fixed bed of 4.50 g HZSM-5 maintained at 482° C. and one atmosphere pressure. The hydrocarbon/water feed simulates the latex feed of Example 3. Liquids were condensed using a cold water condenser; gases were collected over brine. The following table shows the combined hydrocarbon product distribution as determined by gas chromatography.

| Component | Wt % | Component | Wt % |
|---|---|---|---|
| Methane | 0.4 | $C_5$ P + O | 10.8 |
| Ethane | 0.0 | $C_6$ P + O | 2.0 |
| Ethylene | 9.0 | $C_7$-$C_8$ P + O | 3.4 |
| Propane | 2.5 | Benzene | 4.8 |
| Propylene | 16.4 | Toluene | 16.2 |
| i-Butane | 1.2 | Ethylbenzene | 0.1 |
| n-Butane | 0.5 | Xylenes | 15.9 |
| Butenes | 9.1 | $C_9^+$ P + O + A | 7.8 |

EXAMPLE 7

Limonene and water were pumped at 0.6 WHSV and 2.8 WHSV, respectively, over a fixed bed of 4.50 g HZSM-5 maintained at 482° C. and one atmosphere pressure. The hydrocarbon/water feed simulates the latex feed of Example 3. Liquids were condensed using a cold water condenser; gases were collected over brine. The following table shows the combined hydrocarbon product distribution as determined by gas chromatography.

| Component | Wt % | Component | Wt % |
|---|---|---|---|
| Methane | 0.5 | $C_5$ P + O | 0.3 |
| Ethane | 0.0 | $C_6$ P + O | 1.7 |
| Ethylene | 13.0 | $C_7$-$C_8$ P + O | 4.2 |
| Propane | 3.1 | Benzene | 4.7 |
| Propylene | 15.9 | Toluene | 18.9 |
| i-Butane | 1.1 | Ethylbenzene | 0.2 |
| n-Butane | 0.4 | Xylenes | 17.2 |
| Butenes | 5.3 | $C_9^+$ P + O + A | 13.5 |

EXAMPLE 8

Squalene and water were pumped at 0.6 WHSV and 2.8 WHSV, respectively, over a fixed bed of 4.50 g HZSM-5 maintained at 482° C. and one atmosphere pressure. The hydrocarbon/water feed simulates the latex feed of Example 3. Liquids were condensed using a cold water condenser; gases were collected over brine. The following table shows the combined hydrocarbon product distribution as determined by gas chromatography.

| Component | Wt % | Component | Wt % |
|---|---|---|---|
| Methane | 0.2 | $C_5$ P + O | 1.0 |
| Ethane | 0.0 | $C_6$ P + O | 5.0 |
| Ethylene | 6.9 | $C_7$-$C_8$ P + O | 7.5 |
| Propane | 2.9 | Benzene | 4.8 |
| Propylene | 17.0 | Toluene | 16.3 |
| i-Butane | 2.3 | Ethylbenzene | 1.9 |
| n-Butane | 1.0 | Xylenes | 15.0 |
| Butenes | 11.4 | $C_9^+$ P + O + A | 6.7 |

EXAMPLE 9

Natural rubber latex was pumped at 2.3 WHSV into a stainless steel pyrolyzer tube packed with copper turnings and maintained at 664° C. The pyrolysis gases were passed directly through a fixed bed of 1.50 g REY catalyst maintained at 370° C. and one atmosphere pressure. Liquids were collected using a cold water condenser and gases were collected over brine. The following table shows the combined hydrocarbon product distribution as determined by gas chromatography.

| Component | Wt % | Component | Wt % |
|---|---|---|---|
| Methane | 3.5 | $C_5$ P + O | 29.3 |
| Ethane | 0.5 | $C_6$ P + O | 2.7 |
| Ethylene | 3.1 | $C_7$-$C_8$ P + O | 12.2 |
| Propane | 0.8 | Benzene | 3.5 |
| Propylene | 2.6 | Toluene | 12.8 |
| i-Butane | 0.0 | Ethylbenzene | 0.5 |
| n-Butane | 0.0 | Xylenes | 14.8 |
| Butenes | 2.7 | $C_9^+$ P + O + A | 11.0 |

EXAMPLE 10

Methyl abietate (the methyl ester of a $C_{20}$ diterpene resin acid) was pumped at 1.6 WHSV over a fixed bed of 0.75 g PdMgNaY zeolite catalyst maintained at 400° C. and one atmosphere pressure with hydrogen flowing at 30 cc per minute. Liquids were condensed using a cold water condenser and gases were collected over brine. The conversion of methyl abietate was 55%. The following table shows the combined hydrocarbon product distribution as determined by gas chromatography.

| Component | Wt % | Component | Wt % |
|---|---|---|---|
| Methane | 2.4 | $C_5$ P + O | 0.7 |
| Ethane | 0.3 | $C_6$ P + O | 28.2 |
| Ethylene | 0.1 | $C_7$-$C_9$ P + O | 5.1 |
| Propane | 0.7 | $C_{10}$ A | 3.3 |
| Propylene | 0.4 | $C_{11}$ A | 3.2 |
| i-Butane | 0.0 | $C_{12}$ A | 1.0 |
| n-Butane | 0.0 | $C_{13}$ A | 54.5 |
| Butenes | 0.0 | | |

EXAMPLE 11

Methyl abietate was pumped at 2.0 WHSV over a fixed bed of 2.00 g HZSM-5 catalyst maintained at 400° C. and one atmosphere pressure with hydrogen flowing at 30 cc per minute. Liquids were condensed using a cold water condenser and gases were collected over brine. The conversion of methyl abietate was 53%. The following table shows the combined hydrocarbon product distribution as determined by gas chromatography.

| Component | Wt % | Component | Wt % |
|---|---|---|---|
| Methane | 0.1 | $C_5$ P + O | 4.8 |
| Ethane | 0.3 | $C_6$ P + O | 4.3 |
| Ethylene | 1.9 | $C_7$-$C_8$ P + O | 0.1 |
| Propane | 9.0 | Benzene | 5.6 |
| Propylene | 4.5 | Toluene | 13.9 |
| i-Butane | 3.3 | Ethylbenzene | 2.3 |
| n-Butane | 0.7 | Xylenes | 14.6 |
| Butenes | 0.3 | $C_9$-$C_{13}$ A | 34.3 |

EXAMPLE 12

The methyl ester of tall oil rosin was pumped at 4.2 WHSV over a fixed bed of 0.77 g HZSM-5 catalyst maintained at 400° C. and one atmosphere pressure with hydrogen flowing at 23 cc per minute. Liquids were condensed using a cold water condenser and gases were collected over brine. The conversion of the rosin was 49%. The following table shows the combined hydrocarbon product distribution as determined by gas chromatography.

| Component | Wt % | Component | Wt % |
|---|---|---|---|
| Methane | 0.5 | $C_5$ P + O | 1.1 |
| Ethane | 0.3 | $C_6$ P + O | 3.0 |
| Ethylene | 3.1 | $C_7$-$C_8$ P + O | 0.2 |
| Propane | 5.8 | Benzene | 2.7 |
| Propylene | 6.5 | Toluene | 10.6 |
| i-Butane | 5.0 | Ethylbenzene | 2.1 |
| n-Butane | 0.9 | Xylenes | 15.1 |
| Butenes | 0.2 | $C_9$-$C_{13}$ A | 42.9 |

EXAMPLE 13

A sample of dried Euphorbia lathyrus was treated with acetone in a Soxhlet extractor. The acetone was distilled to produce a waxy green residue. This extract was liquified by heating to 80° C. and was then pumped at 17 WHSV over a fixed bed of 1.00 g HZSM-5 catalyst maintained at 450° C. and one atmosphere pressure with hydrogen flowing at 4 cc per minute. Liquids were condensed using a cold water condenser and gases were collected over brine. The conversion of the extract was 49%. The following table shows the combined hydrocarbon product as determined by gas chromatography.

| Component | Wt % | Component | Wt % |
|---|---|---|---|
| Methane | 0.4 | $C_5$ P + O | 0.4 |
| Ethane | 0.2 | $C_6$ P + O | 4.8 |
| Ethylene | 1.1 | $C_7$-$C_8$ P + O | 0.4 |
| Propane | 1.5 | Benzene | 7.7 |
| Propylene | 1.8 | Toluene | 23.9 |
| i-Butane | 0.0 | Ethylbenzene | 4.7 |
| n-Butane | 0.0 | Xylenes | 24.5 |
| Butenes | 0.0 | $C_9$-$C_{13}$ A | 28.7 |

EXAMPLE 14

Corn oil was pumped at 2.4 WHSV over a fixed bed of 0.77 g HZSM-5 catalyst maintained at 400° C. and one atmosphere pressure with hydrogen flowing at 5 cc per minute. Liquids were condensed using a cold water condenser and gases were collected over brine. The conversion of corn oil was 79%. The following table shows the combined hydrocarbon product distribution as determined by gas chromatography.

| Component | Wt % | Component | Wt % |
|---|---|---|---|
| Methane | 0.1 | $C_5$ P + O | 6.9 |
| Ethane | 0.3 | $C_6$ P + O | 2.2 |
| Ethylene | 1.0 | $C_7$-$C_8$ P + O | 0.0 |
| Propane | 10.3 | Benzene | 3.2 |
| Propylene | 2.2 | Toluene | 9.8 |
| i-Butane | 8.4 | Ethylbenzene | 2.7 |
| n-Butane | 3.9 | Xylenes | 10.1 |
| Butenes | 1.9 | $C_9$-$C_{13}$ A | 16.0 |
| | | $C_{14}^+$ P + O + A | 21.0 |

EXAMPLE 15

Peanut oil was pumped at 1.0 WHSV over a fixed bed of 0.94 g HZSM-12 catalyst maintained at 400° C. and one atmosphere pressure with hydrogen flowing at 5.0 cc per minute. Liquids were condensed using a cold water condenser and gases were collected over brine. The conversion of peanut oil was 96%. The following table shows the combined hydrocarbon product distribution as determined by gas chromatography.

| Component | Wt % | Component | Wt % |
|---|---|---|---|
| Methane | 0.2 | $C_5$ P + O | 22.3 |
| Ethane | 0.2 | $C_6$ P + O | 9.5 |
| Ethylene | 2.0 | $C_7$-$C_8$ P + O | 0.2 |
| Propane | 2.0 | Benzene | 0.7 |
| Propylene | 17.5 | Toluene | 2.1 |
| i-Butane | 6.2 | Ethylbenzene | 0.9 |
| n-Butane | 1.3 | Xylenes | 2.8 |
| Butenes | 20.4 | $C_9$-$C_{13}$ A | 7.6 |
| | | $C_{14}^+$ P + O + A | 4.2 |

EXAMPLE 16

Castor oil was pumped at 2.5 WHSV over a fixed bed of 0.77 g HZSM-5 catalyst maintained at 400° C. and one atmosphere pressure with hydrogen flowing at 5.0 cc per minute. Liquids were condensed using a cold water condenser and gases were collected over brine. The conversion of the castor oil was 90%. The following table shows the combined hydrocarbon product distribution as determined by gas chromatography.

| Component | Wt % | Component | Wt % |
|---|---|---|---|
| Methane | 0.0 | $C_5$ P + O | 3.2 |
| Ethane | 0.1 | $C_6$ P + O | 1.6 |
| Ethylene | 0.4 | $C_7$-$C_8$ P + O | 0.2 |
| Propane | 1.8 | Benzene | 10.2 |
| Propylene | 0.8 | Toluene | 21.6 |
| i-Butane | 0.4 | Ethylbenzene | 4.1 |
| n-Butane | 0.0 | Xylenes | 17.0 |
| Butenes | 0.0 | $C_9$-$C_{13}$ A | 28.2 |
| | | $C_{14}^+$ P + O + A | 10.5 |

EXAMPLE 17

Jojoba oil, a straight chain natural ester, was pumped at 1.3 WHSV over a fixed bed of 0.77 g HZSM-5 catalyst maintained at 400° C. and one atmosphere pressure with hydrogen flowing at 5.0 cc per minute. Liquids were condensed using a cold water condenser and gases were collected over brine. The conversion of the jojoba oil was 98%. The following table shows the combined hydrocarbon product distribution as determined by gas chromatography.

| Component | Wt % | Component | Wt % |
|---|---|---|---|
| Methane | 0.2 | $C_5$ P + O | 6.7 |
| Ethane | 0.7 | $C_6$ P + O | 0.0 |
| Ethylene | 0.5 | $C_7$-$C_8$ P + O | 0.1 |
| Propane | 21.9 | Benzene | 6.0 |
| Propylene | 0.9 | Toluene | 17.3 |
| i-Butane | 13.5 | Ethylbenzene | 2.0 |
| n-Butane | 6.2 | Xylenes | 13.2 |
| Butenes | 0.8 | $C_9$-$C_{13}$ A | 7.6 |
| | | $C_{14}^+$ P + O + A | 2.4 |

EXAMPLE 18

Tall oil pitch was pumped at 2.5 WHSV over a fixed bed of 0.77 g HZSM-5 catalyst maintained at 450° C. and one atmosphere pressure with hydrogen flowing at 5.0 cc per minute. Liquids were condensed using a cold water condenser and gases were collected over brine. The conversion of the pitch was 40%. The following table shows the combined hydrocarbon product distribution as determined by gas chromatography.

| Component | Wt % | Component | Wt % |
| --- | --- | --- | --- |
| Methane | 1.4 | $C_5$ P + O | 3.8 |
| Ethane | 0.8 | $C_6$ P + O | 3.6 |
| Ethylene | 1.6 | $C_7$-$C_8$ P + O | 0.0 |
| Propane | 6.9 | Benzene | 2.4 |
| Propylene | 3.3 | Toluene | 9.0 |
| i-Butane | 3.0 | Ethylbenzene | 1.4 |
| n-Butane | 1.9 | Xylenes | 7.4 |
| Butenes | 2.2 | $C_9$-$C_{13}$ A | 5.7 |
|  |  | $C_{14}{}^+$ P + O + A | 45.6 |

What is claimed is:

1. A process for manufacturing liquid hydrocarbons, said process comprising: segregating from a plant or an animal an organic material or a mixture thereof characterized by an effective hydrogen to carbon ratio of about 1/1.0 to 2.2/1.0 and a molecular weight greater than 150, contacting said organic material or mixture at a temperature of 300° to about 650° C. at a pressure of 1 to 50 atmospheres, and at 0.2 to 20 WHSV, with a catalyst consisting essentially of a crystalline aluminosilicate zeolite having an effective pore diameter greater than about 5 Angstrom units, and recovering a liquid hydrocarbon mixture at least 40% of which distills below about 170° C.

2. The process claimed in claim 1 wherein said crystalline aluminosilicate zeolite is rare earth exchanged zeolite Y.

3. The process claimed in claim 1 wherein said crystalline aluminosilicate zeolite has a silica to alumina ratio of at least about 12, a constraint index of about 1 to 12, and a dried crystal density in the hydrogen form not substantially less than about 1.6 grams per cubic centimeter.

4. The process claimed in claim 1 wherein said crystalline aluminosilicate zeolite is ZSM-5.

5. The process claimed in claim 1 wherein said crystalline aluminosilicate zeolite is ZSM-12.

6. The process claimed in claim 1 wherein said segregated organic material or mixture thereof is comprised essentially of a substance selected from the group consisting of natural hydrocarbons, natural resins, and natural glycerides.

7. The process claimed in claim 3 wherein said segregated organic material or mixture thereof is comprised essentially of a substance selected from the group consisting of natural hydrocarbons, natural resins, and natural glycerides.

8. The process claimed in claim 7 wherein said natural hydrocarbon is hevea rubber.

9. The process claimed in claim 7 wherein said natural resin is rosin.

10. The process claimed in claim 7 wherein said natural glyceride is corn oil.

11. The process claimed in claim 8 or claim 9 or claim 10 wherein said crystalline aluminosilicate zeolite is ZSM-5.

12. The process claimed in claim 1 or in claim 3 wherein said contacting step is conducted in the presence of hydrogen.

13. The process described in claim 7 wherein said natural hydrocarbon is segregated from Euphorbia lathyrus.

14. The process described in claim 7 wherein said natural glyceride is corn oil.

15. The process described in claim 7 wherein said natural glyceride is castor oil.

16. The process described in claim 1 wherein said organic material is jojoba oil.

17. The process described in claim 7 wherein said natural hydrocarbon is segregated from a plant of the genus Asclepias (milkweed).

* * * * *